United States Patent [19]

Tsuji et al.

[11] Patent Number: 5,494,873
[45] Date of Patent: Feb. 27, 1996

[54] CHROMIUM-BASED FLUORINATION CATALYST, PROCESS FOR PRODUCING THE CATALYST, AND FLUORINATION PROCESS USING THE CATALYST

[75] Inventors: Katsuyuki Tsuji; Tetsuo Nakajo, both of Kawasaki, Japan

[73] Assignee: Showa Denko K.K., Tokyo, Japan

[21] Appl. No.: 301,881

[22] Filed: Sep. 7, 1994

[30] Foreign Application Priority Data

Sep. 7, 1993 [JP] Japan .................................. 5-222633

[51] Int. Cl.⁶ .................... B01J 23/00; B01J 27/12; B01J 27/132
[52] U.S. Cl. .................... 502/319; 502/224; 502/228
[58] Field of Search .................... 502/319, 224, 502/228, 231, 104, 120; 570/166, 168

[56] References Cited

U.S. PATENT DOCUMENTS

| | | | |
|---|---|---|---|
| 2,005,707 | 8/1932 | Daudt et al. | 260/166 |
| 3,859,424 | 1/1975 | Scherer et al. | 423/472 |
| 3,992,325 | 11/1976 | Knaak | 252/441 |
| 5,155,082 | 10/1992 | Tung et al. | 502/228 |

FOREIGN PATENT DOCUMENTS

| | | |
|---|---|---|
| 2084864 | 12/1992 | Canada . |
| 0502605 | 9/1992 | European Pat. Off. . |
| 0514932 | 11/1992 | European Pat. Off. . |
| 1443197 | 12/1968 | Germany . |
| 2032098 | 1/1971 | Germany . |
| 3910310 | 6/1964 | Japan . |
| 1262946 | 10/1989 | Japan . |
| 592141 | 4/1993 | Japan . |
| 5146680 | 6/1993 | Japan . |
| 603855 | 6/1948 | United Kingdom . |
| 901297 | 7/1962 | United Kingdom . |
| 0955083 | 4/1964 | United Kingdom ................ 570/166 |
| 1113658 | 5/1968 | United Kingdom ................ 570/166 |
| 9213817 | 8/1992 | WIPO . |

*Primary Examiner*—Shrive Beck
*Assistant Examiner*—Fred J. Parker
*Attorney, Agent, or Firm*—Sughrue, Mion, Zinn, Macpeak & Seas

[57] ABSTRACT

A halogenated hydrocarbon having 1 to 4 carbon atoms is brought into contact with hydrogen fluoride in a gaseous phase in the presence of a catalyst prepared by firing a substance composed mainly of chromium(III) hydroxide in the presence of hydrogen at a temperature of 350° to 500° C. or a catalyst prepared by heat-treating the above substance in an inert gas stream at a temperature of 100° to 600° C. and then firing the heat-treated substance in the presence of hydrogen at the above temperature or any one of catalysts prepared by partially fluorinating the above catalysts.

12 Claims, 4 Drawing Sheets

CHROMIUM-BASED FLUORINATION CATALYST, PROCESS FOR PRODUCING THE CATALYST, AND FLUORINATION PROCESS USING THE CATALYST

BACKGROUND OF THE INVENTION

1. Field of the Invention

The present invention relates to a process for producing a chromium-based fluorination catalyst, the obtained fluorination catalyst or catalyst precursor and a fluorination process and more particularly to a process for producing a chromium-based fluorination catalyst which can be used in the production of a halogenated hydrocarbon by a fluorination reaction of a halogenated hydrocarbon having 1 to 4 carbon atoms in a gaseous phase, the obtained fluorination catalyst and a process for fluorinating a halogenated hydrocarbon using said catalyst. Especially, the present invention aims to provide a process for producing a catalyst which can exhibit high activity and selectivity and is useful for the production of hydrofluorocarbons (abbreviated to "HFC") and hydrochlorofluorocarbons (abbreviated to "HCFC") which, in recent years, have been mass-produced as alternative flons.

2. Description of the Related Art

The process for producing a halogenated hydrocarbon containing fluorine from a halogenated hydrocarbon having 1 to 4 carbon atoms and hydrogen fluoride is roughly classified into a gaseous phase process and a liquid phase process. In recent years, a problem of the degradation of the ozone layer by chlorofluorocarbons (abbreviated to "CFC") having in their molecules a chlorine atom(s) has become brought to the fore, and HCFC having hydrogen in its molecule and HFC not having chlorine in its molecule have been proposed as alternatives for CFC (hereinafter referred to as "alternative flons"), and some of them have been already mass-produced. A gaseous phase process is a particularly promising process for the production of these alternative flons. In the gaseous phase process, the selection of the catalyst is important, and various catalysts have been proposed for this purpose up to now.

In patents, various metals such as Cu, Ag, Na, Cd, Ca, Zn, Hg, V, Sb, Mn, Fe, Ni, Co and Pt, for example, in the form of halides supported on activated carbon, are described to be useful as the catalyst (see U.S. Pat. No. 2005707). In many cases, however, a catalyst composed mainly of an oxide, fluoride or oxyfluoride of chromium or a halide of aluminum, iron or other metals is generally used. Especially, it is most common to use a catalyst comprising a chromium oxide, and many production methods and compositions have hitherto been proposed for the chromium oxide catalyst.

Japanese Examined Patent Publication (Kokoku) No. 39-10310 proposes a $Cr_2O_3$ catalyst produced by imprenating alumina with chromic(VI) acid, drying the impregnated alumina and subjecting the dried impregnating Cr (VI) to reduction with hydrogen. Japanese Examined Patent Publication (Kokoku) No. 41-203 describes that a black chromium oxide having an atomic ratio of O to Cr in the range of from 1.5 to 3 produced by repeating several times firing in an oxygen atmosphere and firing in a hydrogen atmosphere and finally carrying out firing in an oxygen atmosphere has a high activity. Further, Japanese Examined Patent Publication No. 42-3004 discloses a $Cr_2O_3$ catalyst produced by firing hydrous chromium oxide, which has been prepared from a chromium(III) salt solution by the precipitation process, in an atmosphere comprising water vapor and an inert gas at 300° to 400° C.

In recent years, Japanese Unexamined Patent Publication (Kokai) No. 5-146680 describes that a catalyst prepared in the same manner as described in Japanese Examined Patent Publication (Kokoku) No. 42-3004, that is, a chromium oxide having a specific surface area of not less than 170 $m^2/g$ prepared by firing a chromium hydroxide, which has been prepared by the precipitation process, in a N2 gas stream at 380° to 460° C. has a high activity.

The present inventors have already found that the selection of heat treatment conditions is important at the time of regeneration of a Cr-based fluorination catalyst. Specifically, as described in Japanese Unexamined Patent Publication (Kokai) No. 5-92141, the activity of the catalyst can be restored sufficiently without scattering of Cr by heat-treating the catalyst first with an oxidizing gas, such as $O_2$, and then with a reducing gas, such as $H_2$.

However, when HCFC and HFC each containing in its molecule a hydrogen atom, which have been proposed as alternative flons, are produced by reacting a halogenated hydrocarbon with hydrogen fluoride, the reaction does not proceed smoothly in many cases as compared with the reaction in the production of the conventional CFC. In this case, in order to attain a satisfactory yield using the conventional chromium-based fluorination catalyst, the reaction should be carried out at a high temperature of 350° C. or above. Further, in the production of a halogenated hydrocarbon having hydrogen in its molecule, the deposition of carbon on the catalyst is so significant that a deterioration in catalytic activity is likely to be accelerated (see Japanese Examined Patent Publication (Kokai) No. 1-262946).

Since the rate of deterioration in catalytic activity increases with increasing the reaction temperature, a reaction at a low temperature using a catalyst having a high activity contributes to thermal energy saving and, at the same time, significantly benefits the catalyst life. For this reason, in order to produce HCFC and HFC with a high efficiency, there are demands for catalysts superior to the conventional fluorination catalyst in catalytic activity and life.

An object of the present invention is to provide a process for producing a chromium-based fluorination catalyst useful for the production of HCFC and HFC and a process for producing a halogenated hydrocarbon having in its molecule a hydrogen atom(s) and a fluorine atom(s) with a high efficiency by fluorinating a halogenated hydrocarbon having 1 to 4 carbon atoms in a gaseous phase using said catalyst.

DISCLOSURE OF THE INVENTION

The present inventors have made extensive and intensive studies with a view to solving the above-described problems and, as a result, have clarified that as with the regeneration of the catalyst, heat treatment conditions at the time of preparation of the catalyst have a large influence on the catalyst performance. It was also found that a chromium-based fluorination catalyst produced, by firing or heating a substance composed mainly of chromium(III) hydroxide in the presence of hydrogen at a temperature of 350° to 500° C. to prepare a precursor of a catalyst and partially fluorinating the precursor of the catalyst in a stream of a gas containing hydrogen fluoride, for example, is superior to the conventional fluorination catalyst in selectivity as well as in activity, which has led to the completion of the present invention.

The present invention relates to a process for producing a chromium-based fluorination catalyst, characterized by comprising the step of firing (i.e., heating) a substance composed mainly of a chromium(III) hydroxide in the presence of hydrogen at a temperature of 350° to 500° C.

The present invention also relates to a process for producing a chromium-based fluorination catalyst, comprising the steps of heat-treating a substance composed mainly of chromium(III) hydroxide in an inert gas stream at a temperature of 100° to 600° C. and then firing the heat-treated substance in the presence of hydrogen at a temperature of 350° to 500° C.

The present invention further relates to a process for producing a chromium-based fluorination catalyst as above, characterized in that said substance is partially fluorinated after the firing in the presence of hydrogen.

The present invention further relates to a process for producing a chromium-based fluorination catalyst as above, characterized in that after the firing in the presence of hydrogen, said substance is partially fluorinated in a gas stream containing hydrogen fluoride at a temperature of 300° to 500° C.

The present invention further relates to a process for producing a chromium-based fluorination catalyst as above, characterized in that the substance composed mainly of chromium(III) hydroxide contains at least one element selected from the group consisting of cobalt, nickel, copper, silver, zinc, cadmium, mercury, aluminum, gallium, tin and lead.

The thus obtained catalyst or catalyst precursor can be defined by that the X ray diffraction exhibits diffraction peaks characteristic or similar to that of crystalline $Cr_2O_3$, said diffraction peaks having a half maximum peak width 1.2 times or more the half maximum peak with of a material obtained by firing a substance mainly composed a chromium (III) hydroxide in a presence of oxygen at 400° C. for 2 hours or more.

Specifically, one of the thus obtained catalysts on catalyst precursors can be defined by that the X-ray diffraction exhibits diffraction peaks characteristic to crystalline $Cr_2O_3$, said diffraction peaks inducing a peak appearing at a spacing of lattice planes in a range of 2.65 to 2.69 Å, said peak having a half maximum peak width of 0.8 degree or more.

The present invention also relates to a process for fluorinating a halogenated hydrocarbon, comprising the step of bringing a halogenated hydrocarbon having 1 to 4 carbon atoms into contact with hydrogen fluoride in a gaseous phase in the presence of a fluorination catalyst as above.

The present invention further relates to a process for fluorinating a halogenated hydrocarbon as above, characterized in that said halogenated hydrocarbon is a hydrogen-containing halogenated hydrocarbon.

DETAILED DESCRIPTION OF THE INVENTION

In the present invention, the chromium(III) hydroxide is a compound which is represented, for example, by the chemical formula $Cr_2O_3 \cdot nH_2O$ and can be prepared from a Cr(III) salt by precipitation or other processes. The n value is usually in the range of from 2 to 4. Suitable examples of the Cr(III) salt include a nitrate, a chloride and a sulfate.

Among them, a nitrate is particularly preferred. The chromium hydroxide by the precipitation process can be prepared by mixing an aqueous Cr(III) salt solution with an aqueous alkali solution to form a precipitate which is then collected by filtration, washed and dried.

When the catalyst is desirably in the form of a molding, the catalyst may be pelletized after drying or extruded before drying to prepare a molding.

The drying temperature is preferably in the range of from 80° to 130° C., particularly preferably in the range of from 90° to 120° C. In this case, the n value is in the range of from 2.5 to 3.5. When drying is carried out in an inert gas atmosphere, the drying temperature may be higher. However, when pelletizing is carried out, the drying temperature is preferably 150° C. or below.

The alkali may be any one so far as it is produced on a commercial scale. Preferred alkalis include ammonia, sodium hydroxide, sodium carbonate, sodium hydrogencarbonate, potassium hydroxide, potassium carbonate, potassium hydrogencarbonate, ammonium carbonate and ammonium hydrogencarbonate. Among them, ammonia is particularly preferred. A particularly preferred method of mixing the aqueous Cr salt solution with the aqueous alkali solution is to simultaneously or alternately add these aqueous solutions dropwise so as to keep the pH of the reaction mixture within 6.9 to 9.

Before the substance composed mainly of the chromium (III) hydroxide is fired in the presence of $H_2$, it may be previously heat-treated at a temperature of 600° C. or below if in an inert gas. Such a heat treatment gives rise to a dehydration reaction or a decomposition reaction of the residual salt, so that the chromium hydroxide is expected to approach a compound represented by the compositional formula $Cr_2O_3$.

In an atmosphere containing $O_2$, the heat treatment cannot be carried out at a temperature of 300° C. or above (the expression "atmosphere containing $O_2$" used herein being intended to mean an atmosphere containing $O_2$ in an amount of not less than 1000 Pa in terms of absolute pressure and typically air). This is because the exposure of chromium hydroxide to a high temperature of 350° C. or more in an atmosphere containing $O_2$ causes the chromium hydroxide to be converted to $Cr_2O_3$ having a small specific surface area, and the small specific surface area, once reduced, cannot be easily recovered.

A high specific surface area is a requirement for a catalyst having a high activity, and the fluorination in the later step causes a further lowering in the specific surface area, and therefore the use of the above precursor having a small specific surface area is disadvantageous. It is desired that the catalyst precursor prior to fluorination has a specific surface area of 150 m²/g or more, more preferably 180 m²/g or more. For this reason, it is preferred to use a chromium hydroxide which has not been exposed to an $O_2$-containing atmosphere, or has been exposed to an $O_2$-containing atmosphere at a temperature of 200° C. or below, preferably 150° C. or below.

Even in the case of a precursor, which has been once fired in $H_2$, firing of the precursor in an $O_2$-containing atmosphere gives rise to problems such as a lowering in specific surface area and partial formation of Cr(VI) which is scattered during fluorination. For this reason, the firing in an $O_2$-containing atmosphere in the final stage, such as is described in Japanese Examined Patent Publication (Kokoku) No. 41-203, should be avoided.

Preferred firing methods include ① a method which comprises raising the temperature of a dried substance composed mainly of a chromium hydroxide to a temperature of 350° to 500° C. in a gas stream containing hydrogen and, at that temperature, firing the substance for a predetermined period of time and ② a method which comprises first heat-treating a dried substance composed mainly of chromium(III) hydroxide in an inert gas stream at a temperature of 100° to 600° C. and then firing the heat-treated substance in a gas stream containing hydrogen at a temperature of 350° to 500° C. for a predetermined period of time.

The substance composed mainly of chromium hydroxide may contain a metal other than Cr, particularly at least one element selected from the group consisting of the elements in the groups 8, 9, 10, 11, 12, 13 and 14 of the Long Periodic Table (new IUPAC rules of nomenclature), which elements are expected to serve as a copromoter. Typically, these metals would be present in the form of metal hydroxides and/or salts. Therefore, the substance composed mainly of chromium hydroxide may be a mixed hydroxide of chromium and other metal(s), a mixture of chromium and other metal hydroxides, or a mixture of chromium hydroxide and other metal hydroxides(s) and/or salt(s). Among others, Co, Ni, Cu, Ag, Zn, Cd, Hg, Al Ga, Sn, Pb and the like are expected to have the effect of accelerating the activity and prolonging the catalyst life when they are contained in an amount in the range of from 0.001 to 0.5, preferably in the range of from 0.003 to 0.3, particularly preferably in the range of from 0.003 to 0.2, in terms of the atomic ratio to Cr.

The addition of the above element can be easily achieved by a method in which a salt of the intended element is added to an aqueous Cr salt solution in a predetermined amount during preparing a chromium hydroxide by the precipitation process, by a method in which a chromium hydroxide is impregnated with an aqueous solution of a salt of the intended element, or by other methods.

The substance as described above is fired in the presence of $H_2$ to prepare a precursor of a catalyst. As described in Japanese Examined Patent Publication (Kokoku) No. 42-3004 and Japanese Unexamined Patent Publication (Kokai) No. 5-146680, a stream of an inert gas, such as $N_2$, has hitherto been considered suitable to an atmosphere for firing in a process for producing a fluorination catalyst.

Nevertheless, according to the present invention, firing in the presence of $H_2$ can provide a catalyst having a higher activity.

When the firing temperature is excessively low, no effect can be attained, while when it is excessively high, there occur problems such as a lowering in specific surface area. For this reason, the firing temperature is suitably in the range of from 350° to 500° C., preferably in the range of from 370° to 460° C., particularly preferably in the range of from 370° to 450° C.

The concentration of $H_2$ in the firing gas may be in the range of from 0.1 to 100% by volume. If necessary, it is also possible for not more than 20% by volume of water to coexist in the gas, and 0.3 to 10% by volume of water vapor may coexist in $H_2$. The presence of $O_2$ in the gas causes a safety problem, so that the $O_2$ concentration should be limited to not more than 0.1% by volume. The gas flow rate is suitably in the range of from 10 to 10000 $h^{-1}$ in terms of GHSV (after conversion to a standard condition basis), and the pressure may range from atmospheric pressure to 10 $kg/m^2G$ from the viewpoint of operation convenience. The firing is carried out under the above conditions for at least 30 min, preferably 1 to 10 hr, thereby preparing a precursor of a catalyst.

The precursor, as such, may be used in the reaction. However, it is preferred that the precursor be subjected to a fluorination treatment prior to use in the reaction. The fluorination may be conveniently carried out in a gaseous phase. In this case, the precursor may be treated in the presence of a gas having a capability of fluorinating the precursor, such as HF, $F_2$ or a hydrocarbon having F in its molecule.

Proper treating conditions, such as temperature, pressure and treatment time, for attaining an intended fluorine content should be selected depending upon the fluorination capability of the gas used.

The fluorination is preferably carried out in a gas stream containing HF. The treatment temperature is preferably in the range of from 300° to 500° C., particularly preferably in the range of from 300° to 450° C. The HF concentration may be in the range of from 1 to 100% by volume. Generation of excessive heat during the treatment has an adverse effect such as a remarkable lowering in specific surface area. In order to prevent this unfavorable phenomena, it is preferred to dilute, if necessary, HF with an inert gas, such as $N_2$, so that the maximum temperature increase (hereinafter referred to as "ΔT") derived from generation of heat is not more than 50° C.

The gas flow rate is suitably in the range of from 10 to 10000 $h^{-1}$ in terms of GHSV. The pressure may range from atmospheric pressure to 20 $kg/cm^2G$. It is preferred for the used HF to have as low a water content as possible. The water content in HF used is preferably not higher than 150 ppm by weight, still preferably not higher than 100 ppm by weight.

One example of a still preferred method of fluorinating a precursor of a catalyst will now be described. HF and $N_2$ are supplied in such a manner that the HF concentration is in the range of from 5 to 30% by volume at 300° to 350° C. under atmospheric pressure and fluorination is initiated. After the hot spot is passed through the packed bed of the precursor, the HF concentration is increased gradually to 90% by volume or higher with caution so as not to cause generation of excessive heat. Subsequently, the pressure is increased, and the treatment is carried out under a pressure of 2 to 10 $kg/cm^2G$ until the heat is not generated any more.

The heat treatment in an inert gas, the firing in the presence of $H_2$ and the fluorination treatment may be conducted in an identical reaction vessel so far as the reaction vessel is made of Inconel or Hastelloy. This is convenient for the operation.

The HF treatment causes the precursor of a catalyst to be partially fluorinated to form a compound or substance with F atoms being included therein. The catalyst should contain O beside F. The content of O is preferably in the range of from 3 to 28% by weight and the content of F preferably be in the range of from 3 to 45% by weight, respectively.

The reason why the activity of the catalyst is improved by firing in the presence of $H_2$ has not been elucidated yet. However, it is noted that as described in Adv. Catal., Vol. 20 page 7, when a chromium hydroxide is fired in $N_2$, the amorphous state is maintained and conversion to $Cr_2O_3$ does not occur up to about 470° C.

On the other hand, when a chromium hydroxide is fired in $H_2$, microcrystallization occurs in a range of 390° to 400° C., suggesting that the presence of $H_2$ accelerates the crystallization.

In fact, as described in the following Examples, chromium hydroxide prepared by precipitation from chromium nitrate and aqueous ammonia is fired in $N_2$ at 400° C., crystalline $Cr_2O_3$ is not formed, whereas the formation of crystalline $Cr_2O_3$, coincident with Eskolaite by the powder X-ray diffraction pattern (ICDD cards, 1988, 38-1479), is confirmed when fired in $H_2$ at the same temperature. Furthermore, when the catalyst precursors, respectively prepared by firing in a $N_2$ gas flow or a $H_2$ gas flow at an identical temperature, are treated with HF under identical conditions, it is confirmed that there is a tendency that the catalyst has a smaller fluorine content when fired in a $H_2$ gas flow than in a $N_2$ gas flow.

It is considered that the catalyst prepared by partial fluoridation of a crystallized chromium oxide is more difficult to be fluorinated and therefore more active than the catalyst prepared by partial fluoridation of an amorphous chromium oxide.

If chromium hydroxide is fired in an $O_2$-containing atmosphere, the crystallization also occurs but it is a rapid crystallization with a high heat generation, so called "glow phenomenon". In this rapid crystallization, the specific surface area of the catalyst precursor is significantly reduced to 50 m²/g or lower. In contrast, when fired in the presence of $H_2$, significant heat generation does not occur and the specific surface area of the resultant catalyst precursor is as large as that when fired in a $N_2$ gas flow, as long as it is not fired at an extraordinarily rapid temperature elevation rate.

As described above, requirements for an active catalyst (catalyst precursor) include crystallization to some extent and a large specific surface area. In other words, the desired structure of a catalyst (catalyst precursor) is an agglomerate of microcrystallites. In a catalyst precursor prepared by firing in the presence of $H_2$ at 350° to 500° C. in accordance with the present invention, the above desired structure of the catalyst precursor can be shown in a powder X-ray diffraction chart (hereinafter after referred to as "XRD pattern"). That is, when the catalyst precursor is chromium oxide the XRD chart exhibits diffraction patterns of crystalline $Cr_2O_3$ and the half maximum peak widths thereof are wider than those of a single crystal $Cr_2O_3$ due to microcrystalline structure. Note that the half maximum peak width here is a true half maximum peak with $\Delta$ (2θ) derived from the sample and excluding the broadening of the peak due to instrumental factors and the like. Nevertheless, if sufficient amounts of additives other than Cr are present the XRD chart may not exhibit the XRD pattern characteristic to crystalline $Cr_2O_3$ depending on the type of the additives. It is therefore not easy to define the catalyst precursor containing additives by the XRD pattern only. Further, the half maximum peak width depends on the measuring conditions and measuring equipment and therefore it is not easy to define the value of the half maximum peak width for a additive-containing catalyst additive. Nevertheless, it can be said that a catalyst precursor should preferably have a half maximum peak width 1.2 times or more, more preferably 1.4 times or more the corresponding half maximum peak width of a catalyst precursor prepared by firing the identical starting substance in an atmosphere containing $O_2$ in an amount of 1% by volume or more at 400° C. under atmospheric pressure for 2 hours or more.

For a catalyst (catalyst precursor) exhibiting the diffraction pattern of crystalline $Cr_2O_3$, for example, a preferred half maximum peak width can be exemplified by a true half maximum peak width (corresponding to (104) plane ICDD card 38-1479) of 0.8 degree or more, more preferably 1.0 degree or more for the diffraction peak appearing at the spacing of lattice planes in a range of 2.65 to 2.69 Å. The measurement of the half maximum peak width is preferably carried out using a unit with a monochrometer under the conditions allowing high resolution, such as a 1 degree/min or less of a scanning speed and a 0.15 mm or less of a width of an X ray receiving slit. It is also required that the spreading of the diffracted rays due to the optical system be corrected, for example, by conducting measurement of a silicon single crystal having a sufficiently large crystal size under the same conditions.

The chromium-based fluorination catalyst may be supported by a conventional support such as $Al_2O_3$, activated carbon, metal fluoride (e.g., $AlF_3$) or may be bonded with a binder such as graphite. However, if a support is used, the advantageous effect of the present invention is small or is not obtained.

The fluorination catalyst of the present invention can be applied to the fluorination of a halogenated hydrocarbon having 1 to 4, particularly 1 to 2 carbon atoms with HF. Especially, it is particularly effective for the fluorination of a hydrogen-containing halogenated hydrocarbon which is difficult to be fluorinated in the presence of the conventional catalyst and causes the catalyst to be deteriorated very rapidly.

The "hydrogen-containing halogenated hydrocarbon" referred to in the present invention is a halogenated hydrocarbon having H in its molecule, and examples thereof include $CHCl_3$, $CH_2Cl_2$, $CH_2FCl$, $CH_3Cl$, $C_2HCl_3$, $C_2H_2Cl$, $C_2H_3Cl$, $C_2HCl_5$, $C_2HF_2Cl_3$, $C_2HF_3Cl_2$, $C_2HF_4Cl$, $C_2H_2Cl_4$, $C_2H_2FCl_3$, $C_2H_2F_2Cl_2$, $C_2H_2F_3Cl$, $C_2H_3Cl_3$, $C_2H_3FCl_2$, $C_2H_3F_2Cl$, $C_2H_4Cl_2$, $C_2H_4FCl$, $C_2H_5Cl$, $C_3H_2Cl_2$ and $C_3HF_4Cl_3$. Further, Cl in the above compounds may be entirely or partially substituted with Br and/or I.

The fluorination of a hydrogen-containing halogenated hydrocarbon typically includes two types or steps of fluorination when the hydrogen-containing halogenated hydrocarbon has an unsaturated bond. For example, a fluorination of $CCl_2$=CHCl proceeds as below:

$$CCl_2=CHCl + 3HF \rightarrow CF_3CH_2Cl + 2HCl \tag{1}$$

$$CF_3CH_2Cl + HF \rightarrow CF_3CH_2F + HCl \tag{2}$$

In the first step, addition reaction of HF to an unsaturated bond and substitution of fluorine for chlorine occurs and in the second step only substitution reaction occurs.

The last chlorine atom is particularly difficult to be substituted by fluorine. In the above example, the first fluorination reaction from $CCl_2$=CHCl (HCC-1120) to $CF_3CH_2Cl$ (HCFC-133a) easily occurs but the second or last fluorination reaction from HCFC-133a to $CF_3CH_2F$ (HFC-134a) is difficult.

The chromium-based fluorination catalyst of the present invention is effective in both fluorination reactions as above, but particularly useful in the second type of fluorination since the second type of fluorination is difficult with a conventional catalyst.

When these hydrogen-containing halogenated hydrocarbons are fluorinated with HF, the catalyst according to the present invention can provide intended compounds in a higher yield than the conventional fluorination catalyst. Further, it has the effect of providing a predetermined yield at a low reaction temperature, which contribute to prolongation in catalyst life.

The catalyst according to the present invention is effective particularly in the fluorination of $CH_2Cl_2$, $CH_2FCl$, CHCl=$CCl_2$ (trichloroethylene), $CF_3CH_2Cl$ (HCFC-133a), $CCl_2=CCl_2$ (perchloroethylene), $CF_3CHCl_2$ (HCFC-123) and $CF_3CHFCl$ (HCFC-124), which fluorination is considered to be a synthetic route in the production of $CH_2F_2$ (HFC-32), $CH_2FCF_3$ (HFC-134a) and $CHF_2CF_3$ (HFC-125) which have recently drawn attractive attention as alternative flons having no risk of the ozonosphere being degraded.

The fluorination reaction may be carried out by fixed bed, fluidized bed, moving bed and other reaction methods. However, the fixed bed reaction method is generally adopted. Proper reaction conditions vary depending upon the reaction. In general, however, the fluorination reaction may be carried out under conditions of a molar ratio of HF to halogenated hydrocarbon in the range of 0.5 to 20, a temperature in the range from 200° to 400° C., a pressure in the range from atmospheric pressure to 20 kg/cm$^2$G (gauge pressure) and a S.V. value in the range from 50 to 100,000 h$^{-1}$.

EXAMPLES

The present invention will now be described in more detail with reference to the following examples and comparative examples, though it is, of course, not limited to these examples only.

In the following examples and comparative examples, the composition of the catalyst is expressed in % by weight of each element contained in the catalyst determined by a chemical analysis. In the reaction examples, the molar ratio in the reaction examples is the molar ratio of HF to halogenated hydrocarbon, S.V. is a value converted to a standard condition, and the pressure is a gauge pressure.

(Catalyst Preparation Example 1)

A solution of 480 g of $Cr(NO_3)_3.9H_2O$ dissolved in 1.2 liters of pure water and 0.3 liter of 28 wt. % aqueous ammonia were added dropwise, with stirring, to a 10-liter vessel containing 600 ml of pure water over a period of about one hour while controlling the flow rates of the two aqueous solutions so as for the pH of the reaction mixture to be maintained in the range of from 7.5 to 8.5. The resultant hydroxide slurry was filtered, and the collected precipitate was thoroughly washed with pure water and dried at 110° C. The valency of Cr contained in the precipitate after drying was measured by polarography. As a result, it was found that at least 98% of Cr had a valency of +3.

Further, the weight loss on ignition to 600° C. was 26%. Therefore, the chromium hydroxide can be represented by the chemical formula $Cr_2O_3.3H_2O$. The solid matter thus obtained was pulverized and mixed with graphite, and the mixture was pelletized by means of a pelletizer. 60 ml of the pellet was packed into a glass firing tube and fired in a $H_2$ gas stream containing 3 vol. % water vapor at 400° C. for 4 hr, thereby preparing a precursor of a catalyst.

Figure 1:
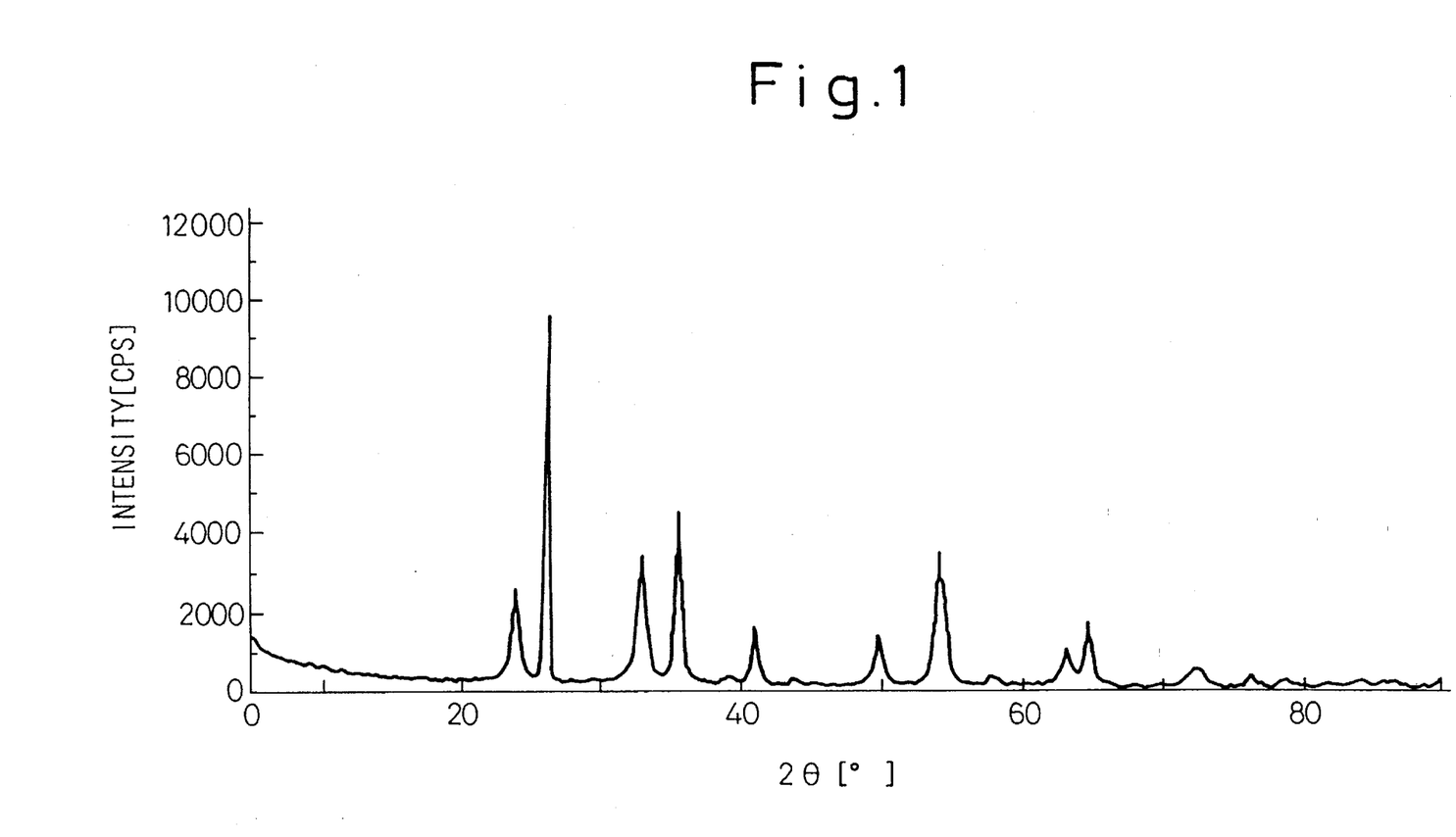
FIG. 1 is an XRD pattern of the catalyst precursor prepared in Catalyst Preparation Example 1.

An XRD pattern of this precursor is shown in FIG. 1. From FIG. 1, it is apparent that crystalline $Cr_2O_3$ is grown. In the X-ray powder diffractometry, a $CuK\alpha_1$ line was used as the X-ray source. The peaks appearing at $2\theta = 26.5°$ and 54.7° are derived from graphite added at the time of molding.

40 ml of the precursor was packed into an Inconel reaction tube and subjected to fluorination first in a 20 vol. % HF gas stream diluted with $N_2$ at 350° C. under atmospheric pressure, then in a 100% HF gas stream not diluted with $N_2$ at 350° C. under atmospheric pressure and finally in a 100% HF gas stream under an increased pressure of 3 kg/cm$^2$G.

The composition of the pellet after the treatment was as follows.

Cr: 60.1%, O: 20.8%, F: 16.5%

(Catalyst Preparation Example 2)

60 ml of a dried pellet prepared in the same manner as in Example 1 for the preparation of a catalyst was packed into a glass firing tube and fired first in a $N_2$ gas stream at 350° C. for 2 hr and then a $H_2$ gas stream at 400° C. for 4 hr, thereby preparing a precursor of a catalyst. The XRD pattern of the precursor has revealed that crystalline $Cr_2O_3$ was grown.

Further, the precursor was fluorinated in the same manner as in Catalyst Preparation Example 1. The composition of the pellet after the treatment was as follows.

Cr: 60.0%, O: 20.6%, F: 16.7%

(Comparative Catalyst Preparation Example 1)

60 ml of a dried pellet prepared in the same manner as in Catalyst Preparation Example 1 was packed into a glass firing tube and fired in a $N_2$ gas stream at 400° C. for 4 hr, thereby preparing a precursor of a catalyst.

Figure 2:
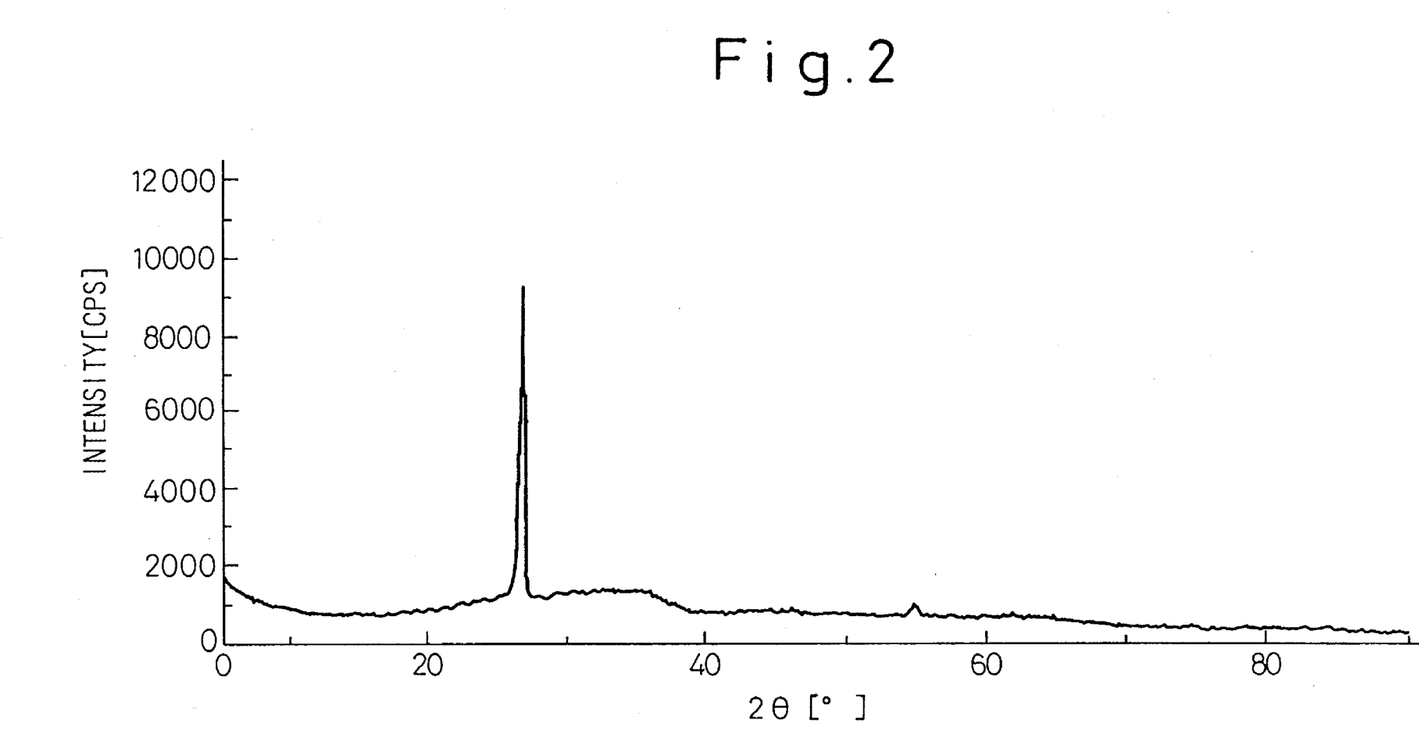
FIG. 2 is an XRD pattern of the catalyst precursor prepared in Comparative Catalyst Preparation Example 1.

The XRD pattern of the precursor is shown in FIG. 2. From the drawing, it is apparent that no crystalline compound is present.

Further, the precursor was fluorinated in the same manner as in Catalyst Preparation Example 1. The composition of the pellet after the treatment was as follows.

Cr: 57.8%, O: 17.3%, F: 22.2%

It is apparent that although the fluorination was carried out under the same conditions as those used in Catalyst Preparation Example 1, the O content is lower and the F content is higher.

(Catalyst Preparation Example 3)

420 g of $Cr(NO_3)_3.9H_2O$ and 5 liters of pure water were placed in a 20-liter reaction vessel to prepare an aqueous Cr solution. 625 g of 10% aqueous ammonia was added dropwise to the aqueous Cr solution with vigorous stirring for a period of 3 min. A precursor was prepared in the same manner as in Catalyst Preparation Example 1, except that the resultant hydroxide slurry was used. The XRD pattern of the precursor has revealed that crystalline $Cr_2O_3$ was grown.

Figure 3:
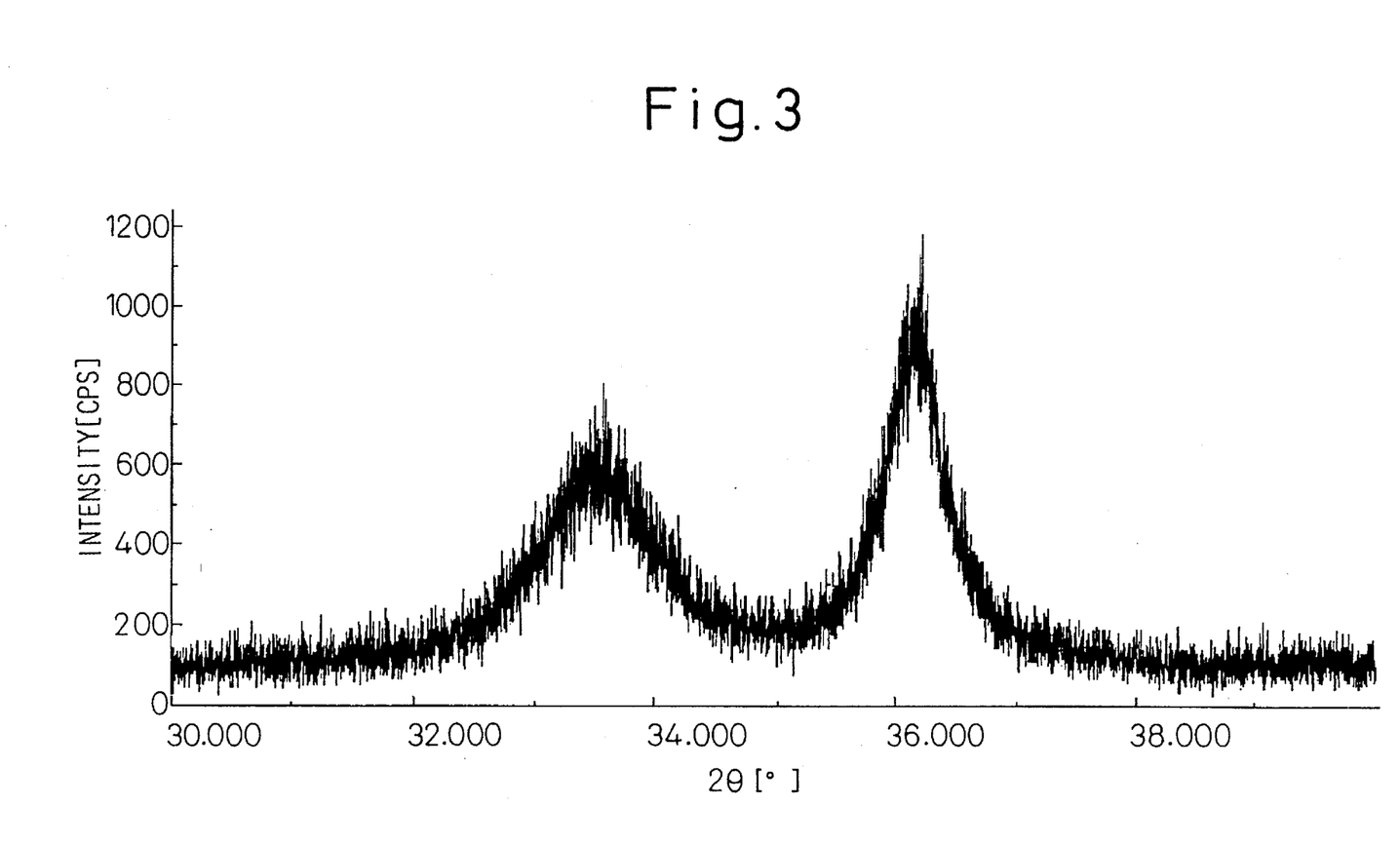
FIG. 3 is an XRD pattern of the catalyst precursor prepared in Catalyst Preparation Example 3.

The half maximum peak width of this precursor in a range of $2\theta=32°$ to 35° was measured under the following conditions. FIG. 3 shows the results. The obtained half maximum peak width was 1.2°. Thus value was obtained after correcting with a value of 0.12° which was derived from the spreading of the X rays due to the optical system in the measuring apparatus and which was obtained from the results of measurement on a single crystal silicon.

The specific surface area of the precursor was also measured to be 210 m$^2$/g.

The conditions for measuring the half maximum peak with:

| | |
|---|---|
| Measuring apparatus: | Rigaku X ray diffraction apparatus RAD-B |
| Output of X rays: | 50 kV - 180 mA |
| Spreading slit: | 1.0° |
| Scattering slit: | 0.5° |
| Ray receiving slit: | 0.15 mm |
| Scanning speed: | 1°/min |

| Step: | 0.002° |
| Measuring mode: | θ-2θ |

40 ml of the precursor was packed into an Inconel reaction tube and subjected to fluorination under atmospheric pressure first in a 20 vol. % HF gas stream diluted with $N_2$ at 360° C. and then in a 100% HF gas stream not diluted with $N_2$ at 360° C. The composition of the pellet after the treatment was as follows.

Cr: 62.3%, O: 24.4%, F: 10.3%

(Comparative Catalyst Preparation Example 2)

60 ml of a dried pellet prepared in the same manner as in Catalyst Preparation Example 3 was packed into a glass firing tube and heated in a $N_2$-diluted air stream ($O_2$ concentration of 2% by volume) under atmospheric pressure with the temperature being raised. When the temperature outside the tube reached around 370° C., the temperature inside the tube suddenly elevated up to about 450° C. After a few minutes, the temperature inside the tube became the temperature almost equal to that outside the tube. After the temperature reached 400° C., that temperature was kept for 4 hours.

The half maximum peak width of the precursor was measured in the same matter as in Catalyst Preparation Example 3.

Figure 4:
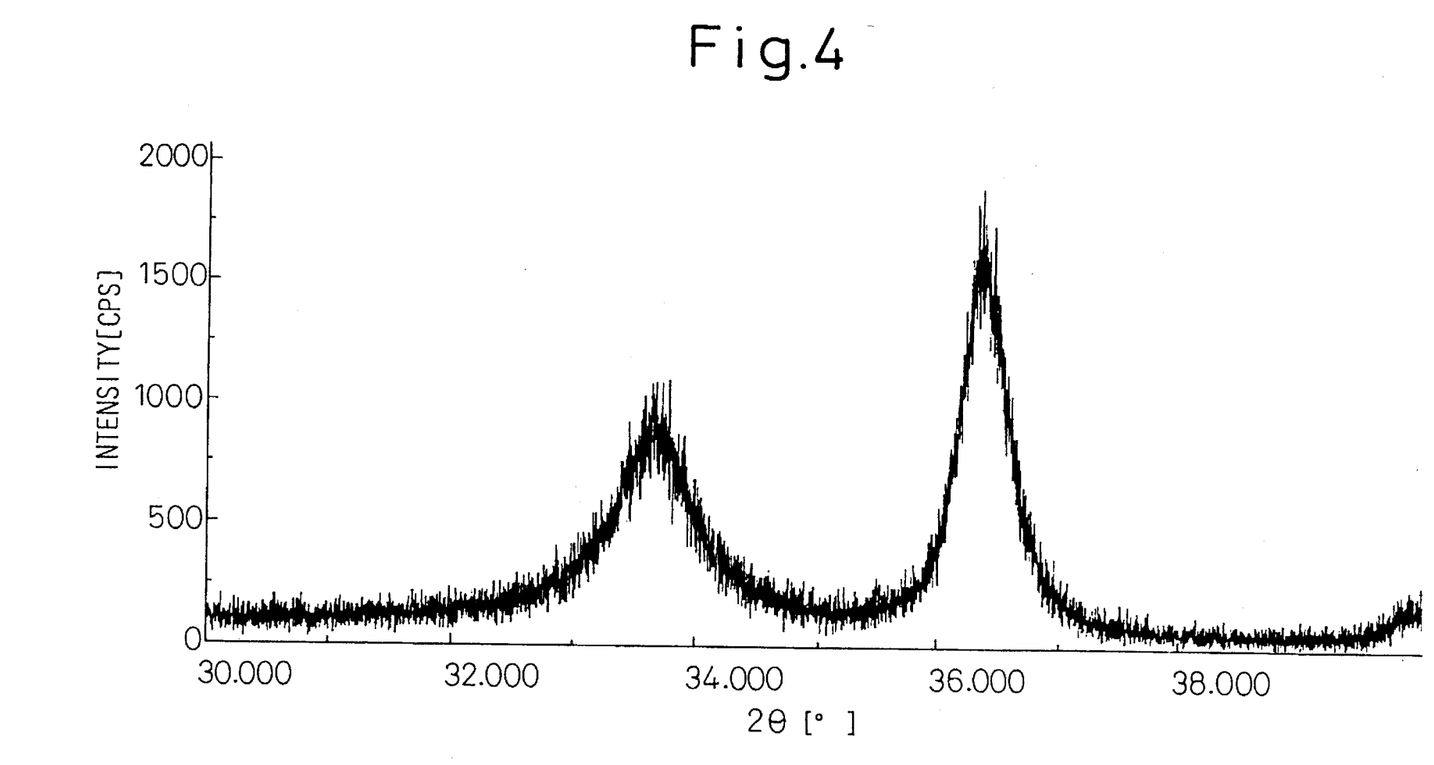
FIG. 4 is an XRD pattern of the catalyst precursor prepared in Comparative Catalyst Preparation Example 2.

The result is shown in FIG. 4. The half maximum peak width of the precursor was 0.7°.

The specific surface area of the precursor was measured to be 36 $m^2/g$.

It is seen when compared the results in Catalyst Preparation Example 3, that the precursor fired in air had a wider half maximum peak width and larger specific surface area than the precursor fired in $H_2$.

(Catalyst Preparation Example 4)

40 ml of a precursor prepared in the same manner as in Catalyst Preparation Example 1 was packed into an Inconel reaction tube and subjected to fluorination under atmospheric pressure first in a flon-13 ($CF_3Cl$) gas stream diluted with $N_2$ at 350° C. and then in a 100% flon-13 gas stream at 350° C. The composition of the pellet after the treatment was as follows.

Cr: 60.4%, O: 23.7%, F: 8.8%, Cl: 3.1%

(Catalyst Preparation Example 5)

A precursor of a catalyst was prepared in the same manner as in Catalyst Preparation Example 1, except that the amount of $Cr(NO_3)_3.9H_2O$ was reduced from 480 g to 432 g and 36 g of $Zn(NO_3)_2.6H_2O$ was additionally used.

The precursor was fluorinated in the same manner as in Catalyst Preparation Example 1.

(Catalyst Preparation Example 6)

A precursor of a catalyst was prepared in the same manner as in Catalyst Preparation Example 1, except that the amount of $Cr(NO_3)_3.9H_2O$ was reduced from 480 g to 432 g and 32 g of $Cd(NO_3)_2.4H_2O$ was additionally used.

The precursor was fluorinated in the same manner as in Catalyst Preparation Example 1.

(Catalyst Preparation Example 7)

A precursor of a catalyst was prepared in the same manner as in Catalyst Preparation Example 1, except that the amount of $Cr(NO_3)_3.9H_2O$ was reduced from 480 g to 432 g and 6 g of $Cu(NO_3)_2.3H_2O$ was additionally used.

The precursor was fluorinated in the same manner as in Catalyst Preparation Example 1.

(Example 8 for Preparation of Catalyst)

A precursor of a catalyst was prepared in the same manner as in Catalyst Preparation Example 1, except that the amount of $Cr(NO_3)_3.9H_2O$ was reduced from 480 g to 432 g and 9 g of $AgNO_3$ was additionally used.

The precursor was fluorinated in the same manner as in Catalyst Preparation Example 1.

(Example 9 for Preparation of Catalyst)

A precursor of a catalyst was prepared in the same manner as in Catalyst Preparation Example 1, except that the amount of $Cr(NO_3)_3.9H_2O$ was reduced from 480 g to 432 g and 9 g of $Pb(NO_3)_2$ was additionally used.

The precursor was fluorinated in the same manner as in Catalyst Preparation Example 1.

(Fluorination Reaction Example 1)

30 ml of the catalyst prepared in Catalyst Preparation Example 1 was packed into an Inconel reaction tube, and a fluorination reaction of trichloroethylene with HF was carried out under the following reaction conditions.

A gas emerging from an outlet of the reaction tube was blown into a trap comprising two phases of an aqueous alkali solution and toluene to remove HF remaining unreacted and the formed HCl, and components extracted into toluene were analyzed by gas chromatography. The results are given in Table 1.

Temperature: 210° C., pressure: atmospheric pressure, molar ratio: 15, S.V.: 1000 $h^{-1}$ (Comparative Fluorination Reaction Example 1)

A fluorination reaction of trichloroethylene was carried out in the same manner as in Fluorination Reaction Example 1, except that the catalyst prepared in Comparative Catalyst Preparation Example 1 was used. The results are also given in Table 1.

TABLE 1

| | Results of fluorination reaction of trichloroethylene | | |
| --- | --- | --- | --- |
| | Conversion of TCE (%) | Selectivity to 133a (%) | Selectivity to 134a (%) |
| Reaction Example 1 | 90.2 | 95.3 | 1.0 |
| Comparative Reaction Example 1 | 66.3 | 70.9 | 0.3 |

In the table, Conversion of TCE, Selectivity to 133a and Selectivity to 134a are respectively the conversion of trichloroethylene, the selectivity to HCFC-133a and the selectivity to HFC-134a.

(Fluorination Reaction Example 2)

30 ml of the catalyst prepared in Catalyst Preparation Example 1 was packed into an Inconel reaction tube, and a fluorination reaction of HCFC-133a with HF was carried out under the following reaction conditions.

A gas emerging from an outlet of the reaction tube was blown into an alkali trap to remove HF remaining unreacted and the formed HCl, and the gas composition was analyzed by gas chromatography. The results are given in Table 2.

Temperature: 320° C., pressure: 2 kg/cm$^2$G, molar ratio: 8, S.V.: 1500 h$^{-1}$ (Fluorination Reaction Example 3)

A fluorination reaction of HCFC-133a was carried out in the same manner as in Fluorination Reaction Example 2, except that 30 ml of the catalyst prepared in Catalyst Preparation Example 2 was used. The results are also given in Table 2.

(Comparative Fluorination Reaction Example 2)

A fluorination reaction of HCFC-133a was carried out in the same manner as in Fluorination Reaction Example 2, except that the catalyst prepared in Comparative Catalyst Preparation Example 1 was used. The results are also given in Table 2. In the table, Yield of 134a and Selectivity to 134a are respectively the yield of HCFC-134a and the selectivity to HCFC-134a.

TABLE 2

Results of flourination reaction of HCFC-133a

| | Reaction temp. (°C.) | Yield of 134a (%) | Selectivity to 134a (%) |
|---|---|---|---|
| Reaction Example 2 | 320 | 19.0 | 99.4 |
| Reaction Example 3 | 320 | 19.1 | 99.3 |
| Comparative Reaction Example 2 | 320 | 16.9 | 99.2 |

(Fluorination Reaction Example 4)

A fluorination reaction of HCFC-133a was carried out in the same manner as in Fluorination Reaction Example 2, except that 30 ml of the catalyst prepared in Catalyst Preparation Example 3 was used and the reaction temperature was 325° C. The results are given in Table 3.

(Fluorination Reaction Example 5)

A fluorination reaction of HCFC-133a was carried out in the same manner as in Fluorination Reaction Example 2, except that 30 ml of the catalyst prepared in Catalyst Preparation Example 4 was used and the reaction temperature was 325° C. The results are given in Table 3.

(Fluorination Reaction Example 6)

30 ml of the precursor of a catalyst prepared in Catalyst Preparation Example 1 was packed into an Inconel reaction tube, and a fluorination reaction of HCFC-133a with HF was initiated under the following reaction conditions, without practicing fluorination of the precursor with HF. The gas composition was analyzed in the same manner as in Fluorination Reaction Example 2.

Temperature: 320° C., pressure: atmospheric pressure, molar ratio: 8, S.V.: 1500 h$^{-1}$ Immediately after the initiation of the reaction, a ΔT of about 50° C. occurred in the catalyst bed, and after that, the generation of heat was gradually reduced. When 10 min has lapsed after the initiation of the reaction, substantially no HFC-134a was formed. However, when 3 hr had lapsed after the initiation of the reaction, HFC-134a was formed in a yield of 5%.

(Fluorination Reaction Examples 7 to 11)

A fluorination reaction of HCFC-133a was carried out in the same manner as in Fluorination Reaction Example 2, except that 30 ml of the catalysts prepared in Catalyst Preparation Examples 5 to 9 were used and the reaction temperature was 315° C. The results are given in Table 3.

TABLE 3

Results of fluorination reaction of HCFC-133a

| | Reaction Tem. (°C.) or Catalyst | Yield of 134a (%) | Selectivity to 134a (%) |
|---|---|---|---|
| Reaction Example 4 | 325 | 19.8 | 99.3 |
| Reaction Example 5 | 325 | 17.0 | 99.0 |
| Reaction Example 7 | Preparation Example 5 | 17.8 | 99.4 |
| Reaction Example 8 | Preparation Example 6 | 16.9 | 99.4 |
| Reaction Example 9 | Preparation Example 7 | 14.5 | 99.2 |
| Reaction Example 10 | Preparation Example 8 | 16.5 | 99.2 |
| Reaction Example 11 | Preparation Example 9 | 15.8 | 99.2 |

In the table, Yield of 134a and Selectivity to 134a are respectively the yield of HFC-134a and the selectivity to HFC-134a.

(Fluorination Reaction Example 12)

30 ml of the catalyst prepared in Catalyst Preparation Example 1 was packed into an Inconel reaction tube, and a fluorination reaction of dichloromethane with HF was carried out under the following reaction conditions. A gas emerging from the outlet of the reaction tube is blown into a heated alkali trap to remove HF remaining unreacted and the formed HCl, and the gas composition was analyzed by gas chromatography.

Temperature: 200° C., pressure: atmospheric pressure, molar ratio: 6, S.V.: 2000 h$^{-1}$ 41% of dichloromethane remained unreacted, and the yields of major products were as follows.

HFC-32: 50%, HCFC-31: 8%

(Fluorination Reaction Example 13)

30 ml of the catalyst prepared in Catalyst preparation Example 1 was packed into an Inconel reaction tube, and a fluorination reaction of perchloroethylene with HF was carried out under the following reaction conditions. A gas emerging from the outlet of the reaction tube was blown into a trap comprising two phases of an aqueous alkali solution and toluene to remove HF remaining unreacted and the formed HCl, and components extracted into toluene were analyzed by gas chromatography.

Temperature: 340° C., pressure: atmospheric pressure, molar ratio: 5, S.V.: 1000 h$^{-1}$ 30% of perchloroethylene remained unreacted, and the yields of major products were as follows.

HFC-125: 5.6%, HCFC-124: 15.5%, HCFC-123: 38.2%

The fluorination catalyst prepared by the process for producing a catalyst according to the present invention has a high activity and, in a fluorination reaction of a halogenated hydrocarbon with HF, enables a desired product to be produced in a high yield. Further, it becomes possible to carry out the reaction at a low temperature, which results in a prolonged catalyst life.

We claim:

1. A process for producing a chromium-based fluorination catalyst, comprising the step of firing a substance composed mainly of a chromium (III) hydroxide in the presence of an H$_2$ gas at a temperature of 350° to 500° C.

2. A process according to claim 1, wherein prior to said step of firing, said process comprises heat treating said substance in inert gas at a temperature of 100° to 600° C.

3. A process according to claim 1, wherein said process additionally comprises partially fluorinating said fired substance.

4. A process according to claim 2, wherein said process additionally comprises partially fluorinating said fired substance.

5. A process according to claim 3, wherein said partial fluorination is carried out in a gas flow containing hydrogen fluoride at a temperature of 300° to 500° C.

6. A process according to claim 4, wherein said partial fluorination is carried out in a gas flow containing hydrogen fluoride at a temperature of 300° to 500° C.

7. A process according to claim 1, wherein said substance further contains at least one element selected from the group consisting of cobalt, nickel, copper, silver, zinc, cadmium, mercury, aluminum, gallium, tin and lead, in an atomic ratio of from 0.001 to 0.5 with respect to chromium.

8. A process according to claim 2, wherein said substance further contains at least one element selected from the group consisting of cobalt, nickel, copper, silver, zinc, cadmium, mercury, aluminum, gallium, tin and lead, in an atomic ratio of from 0.001 to 0.5 with respect to chromium.

9. A chromium-based fluorination catalyst, in which said catalyst or catalyst precursor is prepared in a process as in claim 1, the X ray diffraction of said catalyst exhibits diffraction peaks having a half maximum peak width 1.2 times or more the half maximum peak width of a material obtained by firing a substance identical to the starting substance of said catalyst in the presence of oxygen in an amount of 2% by volume at 400° C. under atmospheric pressure for 4 hours.

10. A chromium-based fluorination catalyst in which the X-ray diffraction exhibits diffraction peaks characteristic to crystalline Cr$_2$O$_3$, said diffraction peaks including a peak appearing at a spacing of lattice of planes in a range of 2.65 to 2.69 said peak having a half maximum peak width of 0.8 degree or more.

11. A chromium-based fluorination catalyst, according to claim 9, wherein said catalyst contains at least one element selected from the group consisting of the elements in the groups 8 to 14 of the Long Periodic Table in an amount of 0.001 to 0.5 in the atomic ratio to Cr.

12. A chromium-based fluorination catalyst, according to claim 10, wherein said catalyst contains at least one element selected from the group consisting of the elements in the groups 8 to 14 of the Long Periodic Table in an amount of 0.001 to 0.5 in the atomic ratio to Cr.

* * * * *